United States Patent [19]

Englert et al.

[11] Patent Number: 5,290,101
[45] Date of Patent: Mar. 1, 1994

[54] LIQUID THERMAL CYCLING METHODS AND APPARATUS

[75] Inventors: Paul J. Englert, Morris Plains; Michael A. Oien, Chatham Township, Morris County, both of N.J.

[73] Assignee: AT&T Bell Laboratories, Murray Hill, N.J.

[21] Appl. No.: 984,807

[22] Filed: Dec. 3, 1992

[51] Int. Cl.⁵ ............... G01N 25/72; G01N 25/00
[52] U.S. Cl. ............... 374/57; 374/141; 73/865.6; 165/61; 165/108; 165/48.1
[58] Field of Search ............ 374/57, 141; 73/865.6; 165/61, 108, 48.1

[56] References Cited

U.S. PATENT DOCUMENTS

| | | | |
|---|---|---|---|
| 4,729,246 | 3/1988 | Melgaard et al. | 374/57 |
| 4,733,973 | 3/1988 | Machak et al. | 374/57 |
| 5,039,228 | 8/1991 | Chalmers | 374/57 |
| 5,167,451 | 12/1992 | Muller et al. | 374/57 |

FOREIGN PATENT DOCUMENTS

| | | | |
|---|---|---|---|
| 0144638 | 7/1985 | Japan | 374/57 |
| 0208760 | 8/1988 | Japan | 73/865.6 |
| 8704526 | 7/1987 | World Int. Prop. O. | 374/57 |

OTHER PUBLICATIONS

"Baised Thermal Shock Liquid System", Thermodynamic, Engineering Management, Feb./Mar. 1991, p. 21.
"Thermal Accelerated Reliability Go-no-go Environmental Testing (TARGET) Dynamic Board Thermal Shock Using a Single Fluid & Bath" by Bradford P. Beaton, NCR Corp., IEEE Sep. 1991.

*Primary Examiner*—Diego F. F. Gutierrez
*Attorney, Agent, or Firm*—Ruloff F. Kip, Jr.

[57] ABSTRACT

Circuit packs to be tested are loaded into first and second test chambers commonly served by a hot liquid reservoir and by a cold liquid reservoir of which both are coupled to both chambers by a liquid handling system containing valves controlled by program determined signals from a controller unit to direct liquid flows as desired between the chambers and reservoirs. During liquid contact periods for the chambers, liquid from the hot reservoir is intermittently pumped into each of the chambers at times different for the two chambers, and liquid from the cold reservoir is intermittently pumped into each of the chambers at times which are different for the two chambers and intervening at each chamber the times of hot liquid pumping thereto, whereby the packs in each chamber are alternately heated and chilled by such liquid so as to be thermally stressed, and the responses of the packs to such stressing are detected. After completion of the liquid contact periods, an air handling system common to both chambers is used to dry the chambers and the packs therein, to reclaim liquid absorbed as vapor in the air during such drying and to cool the dried articles to a comfortable temperature for unloading from the chambers.

17 Claims, 6 Drawing Sheets

LIQUID THERMAL CYCLING METHODS AND APPARATUS

FIELD OF THE INVENTION

This invention relates generally to methods and apparatus for thermally cycling articles by contacting them alternately with hot and cold liquid so as to alternately heat and chill such articles for a useful purpose. More particularly, this invention relates to methods and apparatus of such kind wherein articles are so alternately heated and chilled in order to subject them to environmental stress and to detect the electrical response or responses of such articles to such stress.

BACKGROUND OF THE INVENTION

U.S. Pat. No. 5,039,228 issued Aug. 13, 1991 in the name of Richard M. Chalmers for "Fixtureless Environmental Stress Screening Apparatus" ("Chalmers") discloses apparatus having a single vessel adapted to be alternately filled with liquid from separate hot and cold reservoirs so as to alternately apply such liquid in hot form and in cold form to a device in such chamber to the ends of environmentally stressing such device and detecting how it responds to such stress. The liquid disclosed as utilized to produce such thermal cycling stressing is an aliphatic organic compound (e.g., octane) in which all hydrogen atoms have been replaced by flourine, such compound being a liquid sold under the trademark FLOURINERT, a registered trademark of 3M, and available from the 3M Industrial Chemical Products Division, 3M Center Building 223-6S-04, Saint Paul, Minn. 55144-1000. The Chalmers apparatus is of inefficient design for reason among others that it provides only one chamber for thermocyclic stressing of devices, the result being that the times needed between tests of devices to replace one device by another are down times for the apparatus.

SUMMARY OF THE INVENTION

The foregoing and other disadvantages of the Chalmers apparatus is overcome according to the invention in one of its aspects by providing apparatus for testing articles comprising, means providing first and second chambers for receiving said articles, first and second sources of liquid in hot form and cold form, respectively, liquid handling means comprising piping coupling each of said sources with each of said chambers, pumps disposed in said piping and responsive to control signals to be activated to thereupon produce flows of said liquid through said piping between said sources and chambers, valves in said piping and responsive to control signals to be set to select different paths within said piping for said liquid flows, a controller unit for supplying coordinated control signals to said pumps and valves to produce intermittent flows from said first source of hot liquid into said chambers at times which are different, for, respectively, said first and second chambers, and to produce, also, intermittent flows from said second source of cold liquid into said chambers at times which are different for, respectively, said first and second chambers, and which are also different at each of said chambers than the times thereat of such hot liquid flows so as to environmentally stress articles in said chambers by alternately heating and chilling them by said liquid during test periods respective to said first and second chambers, and means to detect electrical responses of said articles to such stressing.

According to the invention in another of its aspects, the invention is realized by a method for testing comprising, loading a plurality of articles into first and second receptacles, intermittently contacting said articles in said receptacles with hot liquid provided by a source therefor common to both receptacles at times for such hot contacts which are different for, respectively, said first and said second receptacle, and intermittently contacting said articles in said receptacles with cold liquid provided by a source therefor common to both receptacles at times for such cold contacts which are different for respectively, said first and second receptacles, and which are also different at each receptacle than the times thereat of said intermittent contacting of articles therein by said hot liquid so as, thereby, to environmentally stress said articles by alternately heating and chilling each of them by said liquid during respective test periods for said two receptacles, and detecting during said periods responses of said articles to said stressing.

BRIEF DESCRIPTION OF DRAWINGS

For a better understanding of the invention, reference is made to the following description of apparatus and methods which are representative of the invention, and to the accompanying drawings wherein:

FIG. 7 is a flow diagram of the method just referred to;

Figure 1:
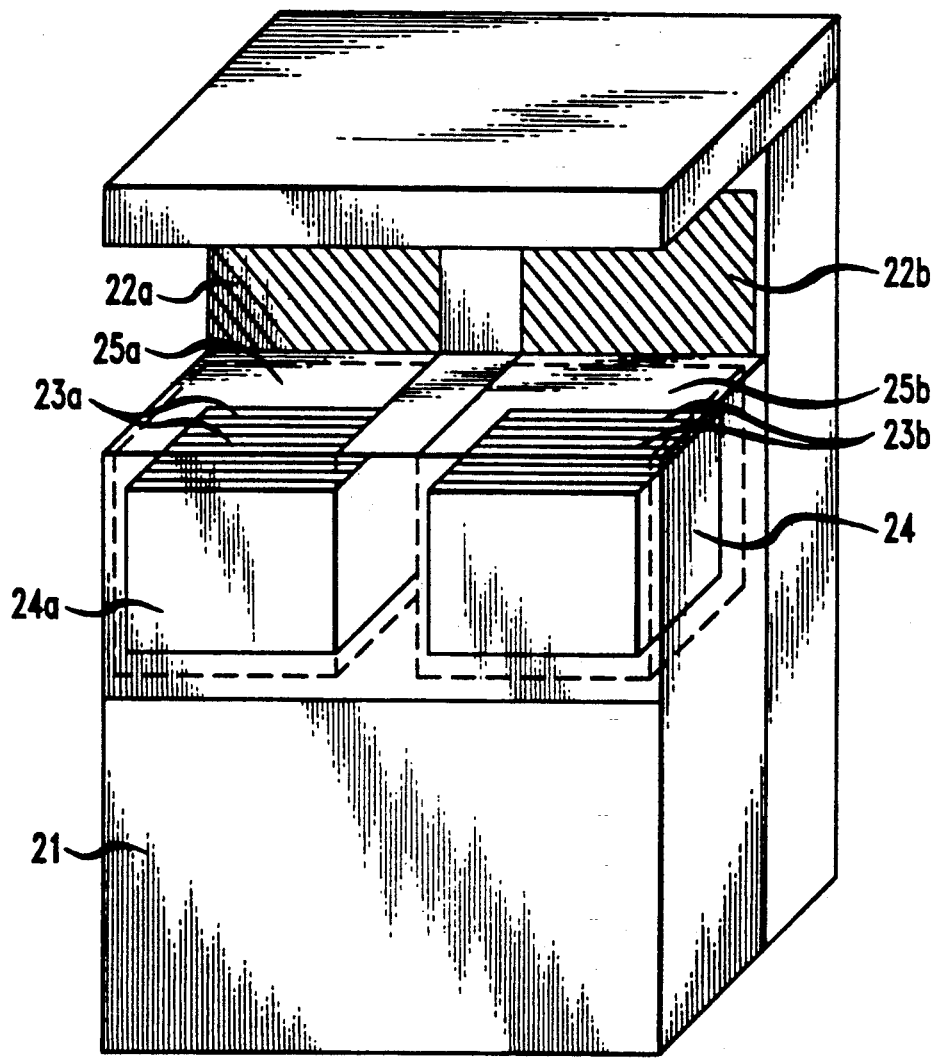
FIG. 1 is a schematic isometric diagram of certain features of an apparatus which is an exemplary embodiment of the invention.

In the description which follows, elements which are counterparts will be designated by the same reference numerals with different alphabetical suffixes being used to differentiate such elements, and it is to be understood that a description hereinafter of any one such element is, unless its context otherwise indicates, to be taken as being equally applicable to any counterpart(s) of that element.

DETAILED DESCRIPTION

Referring now to FIG. 1, the reference numeral 20 designates thermal cycling testing apparatus having a housing 21 enclosing first and second test chambers 25a and 25b. Access to those chambers is provided through top openings therefor made by movement to up position of two chamber doors 22a and 22b which are gasketed to provide when closed respective fluid tight seals for these chambers when the doors are moved to down position to close such openings. The chambers 25 serve as receptacles for articles received therein and introduced into the chambers when their doors 22 are open.

While the invention is not limited to the testing of only one kind of articles, apparatus 20 is designed to receive in chambers 25a and 25b respective groups of circuit packs 23a, 23b comprising printed wiring boards and attached face plates. Within the chambers 25, the circuit packs 23 are held within respective fixtures 24a, 24b for those packs.

Figure 2:
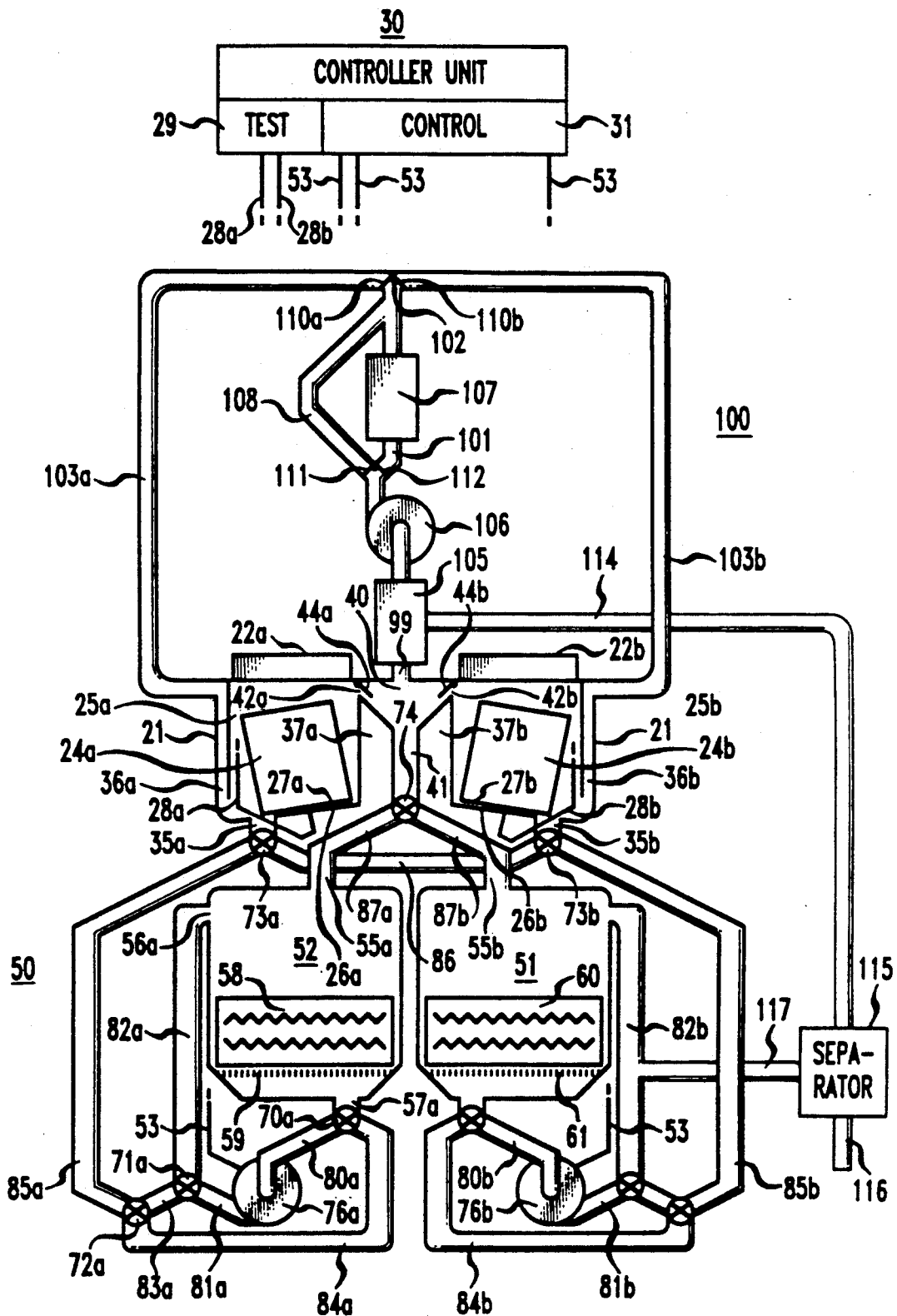
FIG. 2 is a schematic diagram of details of the FIG. 1 apparatus.

Turning now to FIG. 2 and focusing attention on the chamber 25a and its contents, the circuit pack container 24a in that chamber constitutes a test fixture detachably mounted in the chamber and resting on a tilted support surface 26a so that the fixture is at a slant to the horizontal. The circuit packs in chamber 25 are loaded into and unloaded from fixture 24a at respectively, at the beginning and end of a cycle of operation for chamber 25. the packs are loaded into the fixture with their face plates upward, and the fixture on its lower side has a backplane 27a to which all the packs loaded into the fixture are electirically connected, and the backplane connections for those packs are interconnected through cabling 28a to the test section 29 of a controller unit 30 having also a control section 31. Cabling 28a passes out of chamber 25a through a sealed notch (not shown) located in or near the chamber door 22a.

The chamber 25a has at its bottom a port 35a for flow in and out of liquid which in the exemplary apparatus 20 is FLOURINERT. On the chamber's outer side, near its bottom, there is an inlet 36a to the chamber for gas which, in the exemplary apparatus 20, is air.

The chambers 25a and 25b are disposed within respective enclosures 37a, 37b on horizontally opposite sides of an enclosed exhaust space 40 common to both chambers and having at its bottom a pipe 41 for liquid. Those two chambers on their inner sides and at their tops have respective outlets 42a, 42b to space 40 which are vertically above the chambers' gas inlets 36 to be diagonally offset from those inlets, and which outlets are for fluid constituting either liquid in those chambers or gas therein. For liquid pumped into the chambers, outlets 42 serve as weirs by which the liquid at the chamber tops is drawn off by flow of the liquid over the weirs and down the steeply sloping walls of space 40 to its pipe 41.

Figure 3:
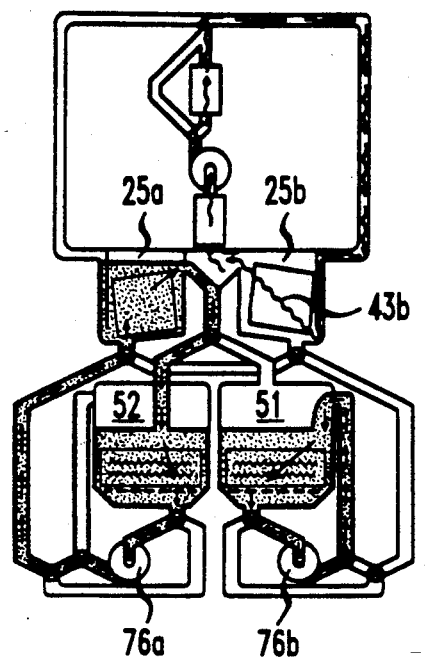
FIGS. 3–6 are diagrams of process steps occurring in the FIG. 2 apparatus in the course of its use to practice a method according to the invention.

For gas in, say, chamber 25a, the outlet 42a in conjunction with with gas inlet 36a defines in the chamber a diagonal path (see corresponding path 43b in FIG. 3) for flow therethrough of gas. As shown (FIG. 2), the backplane 26a on the bottom of test fixture 24a is to one side of that path so as to not block gas flow therein, but part of the fixture and the circuit packs 23a held therein are interposed in that diagonal path so that gas in the path will flow over and make contact with the exteriors of those packs. To control the gas flow, the opening of outlet 42a for chamber 25a can be opened and closed by movement of a gas cut-off valve in the form of damper 44a. The outlet 42b for chamber 25b is similarly equipped with a damper 44b.

Associated with the chambers 25 is a liquid handling system 50 comprising reservoirs 51 and 52 for hot FLOURINERT liquid and cold FLOURINERT liquid, respectively, an arrangement of piping coupling those reservoirs with the chambers 25, and various valves for controlling the flow of FLOURINERT in such piping. The hot reservoir 51 commonly serves both of chambers 25a and 25b. Similarly, the cold reservoir 52 commonly serves both of those chambers. The valves included in system 50 are all valves each having three flow directing settings and responsive to control signals transmitted from control section 31 of unit 30 over conductors 53 to be adjusted to any selected one of those settings to produce a corresponding desired path for flow of FLOURINERT through such system.

Cold Reservoir 52 has inlets 55a and 56a at, respectively, its top and high on its upper side, and has at its bottom an outlet 57a at which is located a valve 70a. Disposed in reservoir 52 between those inlets 55a, 56a and outlet 57a are a chiller 58 and a screen 59 which are adapted to perform the respective functions of cooling FLOURINERT circulating in reservoir 52 and removing contaminants from that circulating liquid. The hot reservoir 51 includes a heater 60 for heating liquid flowing through the reservoir and a screen 61 for removing contaminants therefrom.

A liquid pump 76a is connected by an intake pipe 80a to a first of the ports of valve 70a and is connected by a discharge pipe 81a to (a) a first of the ports of three way valve 71a of which its other ports are connected to (b) a liquid recirculating pipe 82a terminating at inlet 56a, and (c) a shunt pipe 83a terminating at a first port of another three way valve 72a for which there is the exemplary showing of cabling 53 from control unit 30 being connected thereto.

The second port of valve 72a is connected via a bypass pipe 84a to a second port of valve 70a, while the third port of valve 72a is connected via feed pipe 85a to a first port of a three way valve 73a having a second port connected to a pipe 35a of test chamber 25a.

The third port of valve 73a is coupled via a cross connect pipe 86 to the corresponding port of a three way valve 73b at the pipe 35b of the second test chamber 25b, the pipe 86 being used in conjunction with the flow of liquid from both reservoirs. Also common to both of reservoirs 51 and 52 is the arrangement consisting of three way valve 74 and pipes 87a and 87b connecting first and second ports of valve 74 to the respective inlets 55a and 55b of cold and hot reservoirs 52 and 51, the third port of valve 74 being connected to the pipe 41 for exhaust space 40.

The apparatus 20 includes not only the liquid handling system 50 but also a gas handling system 100 (the gas here being air) comprising active components and ducting for coupling for gas flow purposes those active components with each other and with the test chambers 25. System 100 in its layout comprises (FIG. 2) a central path 101 extending from a gas outlet 99 for exhaust space 40 to a duct junction 102 and, also, first and second side paths 103a, 103b provided by ducts 103a, 103b extending from junction 102 to, respectively, the gas inlet 36a of first test chamber 25a and the gas inlet 35b of second test chamber 25b. The central path 101 includes, in the order named from outlet 99 to duct 102, an air chiller 105, an air blower 106 and an air heater 107, the blower being oriented to force air in the direction from space 40 to the mentioned duct junction. The heater 107 can be bypassed for purposes of that air flow by routing the air through a duct 108 shunting the heater. Control over the flow of air in handling system 100 is obtained by air flow regulating means incorporated in the system and including dampers 110a, 110b at the openings of ducts 103a 103b to junction 102 and dampers 111, 112 disposed in central path 101 ahead of heater 107 to direct the flow of air in that path 101 either through the heater or through the shunt path 108 around the heater. The previously described dampers 44 at the outlets 42 of chambers 25 to exhaust space 40 may also be considered to be parts of the gas handling system 100.

The chiller 105 is connected by a pipe 114 to a separator 115 adapted to receive liquid condensed out of the air by the chiller and to process that condensed liquid so as to separate from it any water or other contaminants which may have been picked up by the FLOURINERT in the course of its use. The contaminant water or other matter may be discharged from separator 115 via a pipe 116 while the repurified liquid is returned to hot reservoir 51 via a pipe 117 connected to the recirculating pipe 82b for that reservoir.

All of the mentioned valves and dampers are responsive to control signals supplied thereto via individual cables 53 from control section 31 of controller unit 30 to be adjusted to the settings of these valves and dampers which are, in effect, specified by those signals. Other elements of apparatus are also controlled by signals transmitted from that control section. More specifically, in the course of operation of apparatus 20, the controller unit 30 controls the functioning in apparatus of at least the following: its valves, pumps, dampers, air blower, air heater and chiller, the heater and chiller in, respectively, the hot and cold reservoirs, and the pneumatic sealing of the access doors 22 to the chambers 25. Moreover, the unit 30 operates by way of the cables 28 extending between its test section 29 and the test fixtures 24 in chambers 25 to control the energization of the circuit packs 23 under test in those fixtures, and to detect via signals through those cables the electrical responses of interest of those circuit packs to environmental stressing thereof in the test chambers. The list just given of the functions performed by unit 30 is not necessarily exhaustive. The controller unit is a programmable means operations of which are guided by computer programs.

DETAILS OF USE AND METHODS

Figure 7:
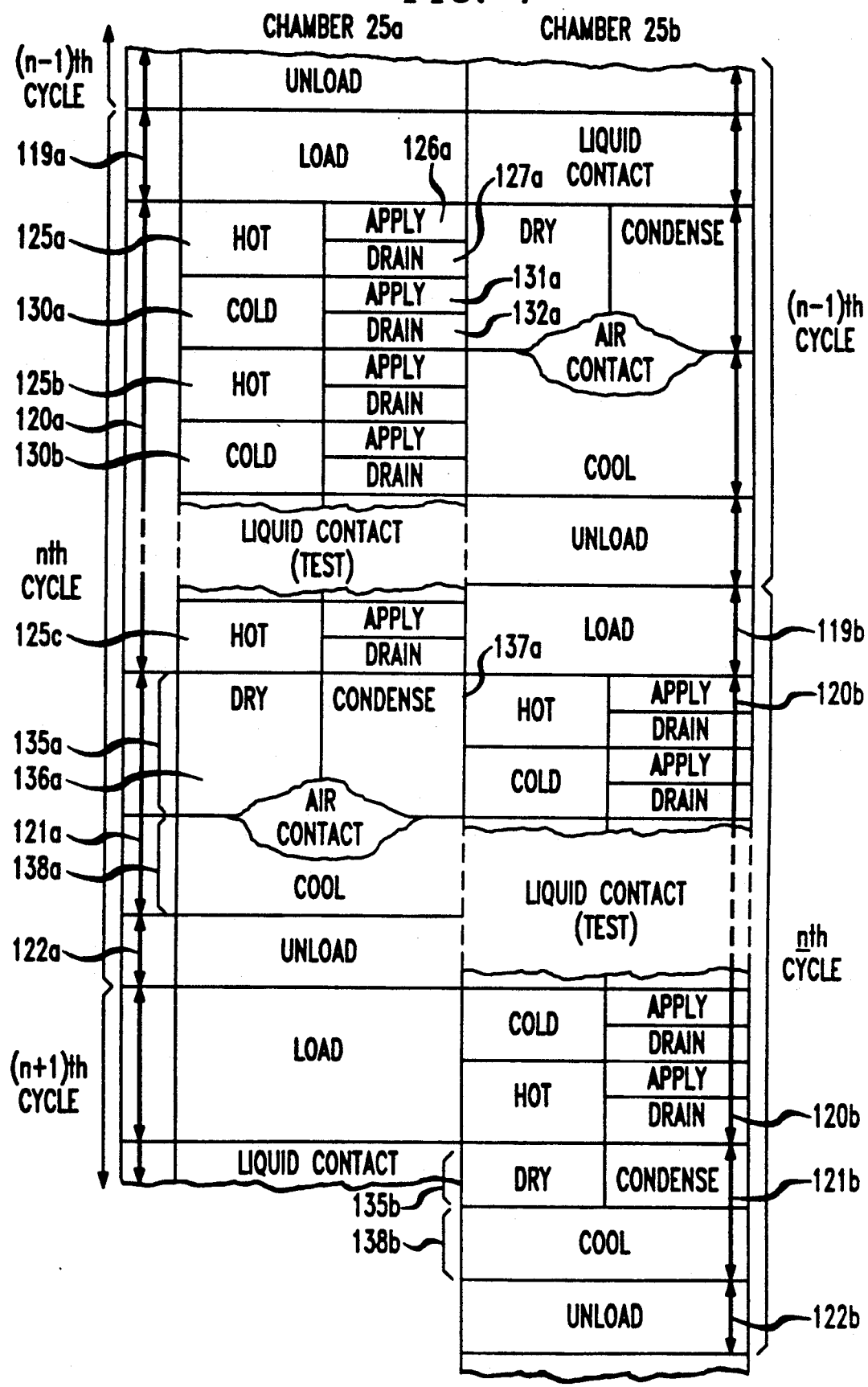

FIG. 7 shows aspects of a method which is utilized to subject the described circuit packs to environmental stress and test their response thereto and which is realized by the operation of apparatus 20 when appropriately programmed to carry out that method. Referring to that figure, each of the first and second test chambers 25a and 25b functions to permit testing of circuit packs or other workpieces over a number of similar cycles of operation, the n th such cycle being shown in full for chamber 25a and chamber 25b. For chamber 25a the n th cycle is divided into an initial service period 119a during which the circuit packs 23a are loaded into the test fixture 24a and the door 22a to chamber 25a is then closed, a liquid contact or test period 120a during which the loaded circuit packs are environmentally stressed by being alternately contacted by hot and cold FLOURINERT thereby, and responses to such packs to such stressing are detected, an air contact period 121 during which the circuit packs 23a in chamber 25a are dried by passage of hot air through the chamber and the packs are then cooled down by passage of cool air through the chamber, and a final service period 122a during which the chamber door 22a is opened and the packs are unloaded from the test fixture and removed from the chamber.

The nth operation cycle for chamber 25b is similar to the one just described except that it lags by one half cycle the nth cycle for chamber 25a.

The events occurring in each period in each operation cycle are program determined and are orchestrated by coordinated control signals transmitted from unit 30 via cables 53 to the elements of apparatus 20 controlled by such signals, and, also, by signals exchanged via cables 28 and test fixtures 24 between the circuit packs 23 and the test section 29 of the controller unit. As shown in FIG. 7 for the (n−1) th and nth cycles for chamber 25b, the unload period of a cycle and the load period of the next cycle add back-to-back to form a service interval straddling both cycles. The various cycle periods depicted in FIG. 7 may each include one or more idle times of greater or lesser length intervening active method steps occurring during such periods.

During the test or liquid contact period 120a of chamber 25a, there occurs an alternation in time of hot phases 125 and of cold phases 130, starting with hot phase 125a and ending with a hot phase 125c, the period preferably always ending with a hot phase. The number of hot and cold phases in period 120a depends on the nature of the articles to be tested and the nature of the test(s) to be performed.

Figure 5:
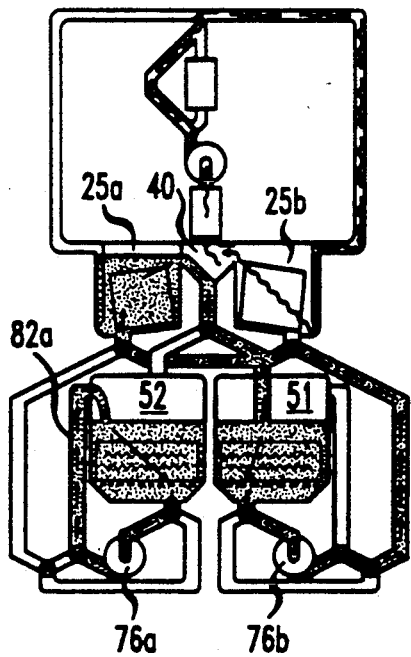
Figure 6:
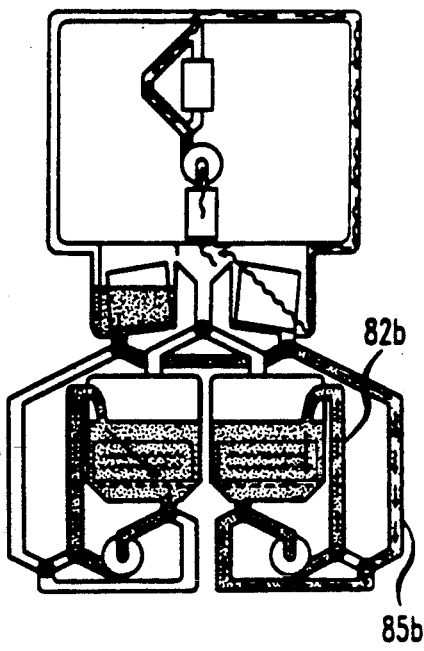

The events occurring during hot phase 125a are graphically depicted in the lower portions of FIGS. 5 and 6 dealing with liquid flow. During a first time interval in phase 125, hot FLOURINERT from hot reservoir 51 is (FIG. 5) pumped by pump 76b to flow into and upward through chamber 25a so as, first, to contact and heat the packs 23a in fixture 24a in that chamber and, next, to overflow into exhaust space 40 and drain from that space back into the hot reservoir. Those events constitute the step 126a of applying hot liquid to the articles 23a. Concurrently, the FLOURINERT in cold reservoir 52 is pumped by pump 76a in a recirculating flow from the reservoir's bottom through the pump and pipe 82a to the reservoir's top and then down through the reservoir past chiller 58 therein to be rechilled by the chiller.

During a next pipe step 127a in hot phase 125a, the recirculation of the cold FLOURINERT through its reservoir 52 is continued while the pump 76b is activated (FIG. 6) to (a) pipe hot FLOURINERT in chamber 25a by suction action via pipe 85b back into the hot reservoir 51, and to (b) commence recirculation via pipe 82b of the hot FLOURINERT through that reservoir. The draining of the hot FLOURINERT from the circuit packs 23a in test fixture 24a in chamber 25a is promoted by the features that (c) the hot liquid can drain freely from the packs without being obstructed by the test fixture's back plane 27a because such backplane is to one side of the drainage path, and (d) the fixture 24a and packs 23a are at a tilt to the horizontal so that the liquid can run down hill.

Figure 4:
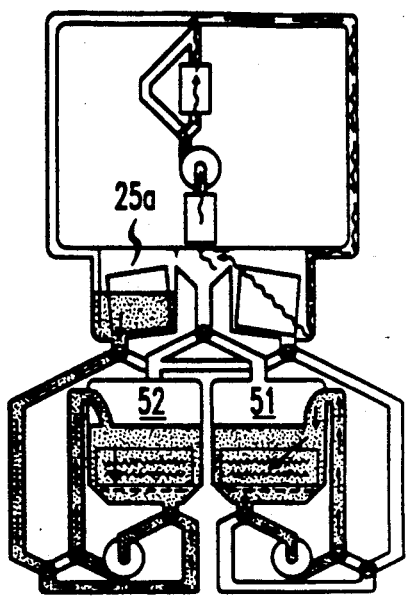

The hot phase 125a for chamber 25a is followed by a cold phase 130a for that chamber divided into an initial cold liquid applying step 131a and a subsequent cold liquid draining step 132a. The events occurring during steps 131a and 132a are shown in the lower portions of FIGS. 3 and 4 dealing with liquid flow. Upon reversing each of the earlier referenced to hot FLOURINERT and cold FLOURINERT by a reference to the other of them, those events are, essentially the same as earlier described as occurring during steps 126a and 127a. That is, during applying step 131a, cold liquid from reservoir 52 is pumped (FIG. 3) by pump 76a up through chamber 25a to contact and chill articles 23 and to then overflows the chamber and drain back through exhaust space 40 into that reservoir while, meanwhile, hot liquid is being recirculated by the action of pump 76b through reservoir 51 to flow by heater 60 and be reheated. During drain step 132a (FIG. 4) the cold liquid is drained from chamber 25a, recirculation of the hot liquid in reservoir 51 is continued, and recirculation of the cold liquid through the reservoir 52 is commenced.

The alternate heating and chilling of the packs 23a during liquid contact period 120a environmentally stresses those packs. The stressed packs are tested during such period by detecting at test section 29 of controller unit 30 various signals supplied to that section, via cables 28a and text fixture 24a, from packs 23a and representing responses of those packs to such stressing. At section 29, those signals are processed to yield the test information desired.

The liquid contact period 120a is followed (FIG. 7) by the air contact period 121a which is divided into a dry-condense phase 135a and a following cooling phase 138a. The period 121a is, except for the test chamber and associated elements involved, the same in respect of the events occurring therein as the air contact period 121b for chamber 25b which is depicted in the upper portions of FIGS. 3 and 4 dealing with air flow, and which period 121b will now be considered.

During the dry-condense phase 135b of period 121b, the dampers 42 and 110 (FIG. 2) are set by signals from controller unit 30 to positions at which air pressurized by blower 106 and heated by heater 107 is guided to flow through side path 103b to gas inlet 36b of chamber 25b and, within that chamber, in diagonal path 43b (FIG. 3) to outlet 42b of the chamber. The hot air flowing through chamber 25 performs the step 136b of drying the chamber 25b and the packs 23b therein of FLOURINERT left in the chamber 120 by converting that liquid into vapor contained in the hot air. The drying of the packs is promoted by the fact that they are interposed in diagonal path 43b, and that the flow of air in that path is not obstructed by backplane 27b of test fixture 24b because such backplate is positioned to one side of the path.

The air containing the FLOURINERT vapor continues in its flow from the outlet 42b of chamber 25b through exhaust space 40 and its outlet 99 to the chiller 105 and then back into the blower 106 to be recirculated around the closed loop comprising the central air path 101 and the side path 103b. Chiller 105 chills the air passing through it so as to perform, concurrently with the drying step 136a, the condensing step 137a of converting the FLOURINERT vapor in the air back into liquid form. That reclaimed liquid is reinserted via pipe 114, separator 115 and pipe 117 back into the liquid handling system 100 of apparatus 20.

The drying, as described, of packs 23b in chamber 25b heats them so that they may be too hot to handle. Accordingly, the dry-condense phase 135b of air contact period 121b is followed by an article cooling phase 138b which is depicted by the upper portions of FIGS. 5 and 6 dealing with air flow. For the purpose of that phase, dampers 111, 112 (FIG. 2) are set by control signals from unit 30 to guide the air from blower 106 to flow through the duct 108 around heater 107 instead of passing through the heater. Since such air has been chilled by passing through chiller 105, the air on reaching chamber 25b cools the packs 23b therein until they can be comfortably handled, at which time the cooling step is ended.

The cooling step 138a of the air contact period 121a for chamber 25a is, except for the chamber and associated elements involved, the same as the step 138b just described.

In connection with the foregoing, it is to be noted that, whether the air moves through chamber 25a in period 121a or through chamber 25b in period 121b, the air recirculates around a closed loop and, otherwise, the apparatus 20 is sealed to reduce to a minimum any leakage therefrom of gaseous or liquid fluid therein except for such contaminants as may be chosen to be withdrawn off from time to time from separator 115 through pipe 116. To have apparatus 20 so sealed against leakage is advantageous because it conserves the expensive FLOURINERT and minimizes the exposure of personnel to that substance.

The cooling step 138a is followed by the step occurring during service period 122a of opening the door 22a of chamber 25a and removing the packs 23a therein from fixture 24a and the chamber. The performance of that unloading step completes the nth cycle of operation for chamber 25a. During the service interval spanning the loading and unloading steps for chamber 25a, the damper 44a is kept closed to isolate the chamber from exhaust space 40 and thus permit the steps occurring in liquid contact period 120b for chamber 25b to proceed without vapor from such liquid leaking from that chamber through space 40 into chamber 25a and then out the open door 22a. For like reason, the damper 44b for chamber 25b is kept closed during the service interval spanning the loading and unloading steps for that chamber.

Comparing the respective cycles of operation for the chambers 25a and 25b, it is to be noted that the hot liquid intermittently contacts the packs 23a in chamber 25a at different times than it contacts the articles 23b in chamber 25b, and that the cold liquid intermittently contacts packs 23a in chamber 25a at times which are different than those at which it contacts the packs 23b in chamber 25b, and which times of cold liquid contact of the packs 23a and 23b are also different than the times of their hot liquid contact but are related thereto so that each of the packs 23a and 23b is alternately heated and chilled by contact with hot liquid and cold liquid during liquid contact periods 120a and 120b. In the FIG. 7 method those two periods do not overlap in time so that the hot and cold liquid contacting of articles is confined to only one at a time of the chambers 25a and 25b. Similarly, the air contact period for chamber 25a does not overlap in the FIG. 7 method with the air contact period for chamber 25b so that the forcing of air through the chambers is restricted to one at a time of the chambers 25a and 25b. While, however, the liquid contact steps are occurring in, say, chamber 25a, other method steps are occurring in chamber 25b, and conversely, so that, even though there may be idle times in the operation cycles of the two chambers, those idle times are reduced because there will be portions in the respective cycles for both chambers in which active method steps will be concurrently taking place in both chambers. The apparatus and methods described above are thus advantageous in relation to techniques wherein different method steps belonging to two cycles of operations with the same method steps do not take place at different places at the same time. Also the apparatus and methods described therein are advantageous in that by having the hot and cold reservoirs 51 and 52 and the gas handling system 100 commonly serve each of the chambers 25a and 25 but at different times, those reservoirs and gas handling means are not required to have any greater capacity than only that needed just to serve a single chamber and, nonetheless, obtain the greater rate of throughput per unit time of articles 23 tested which comes with the use of two chambers.

Figure 8:
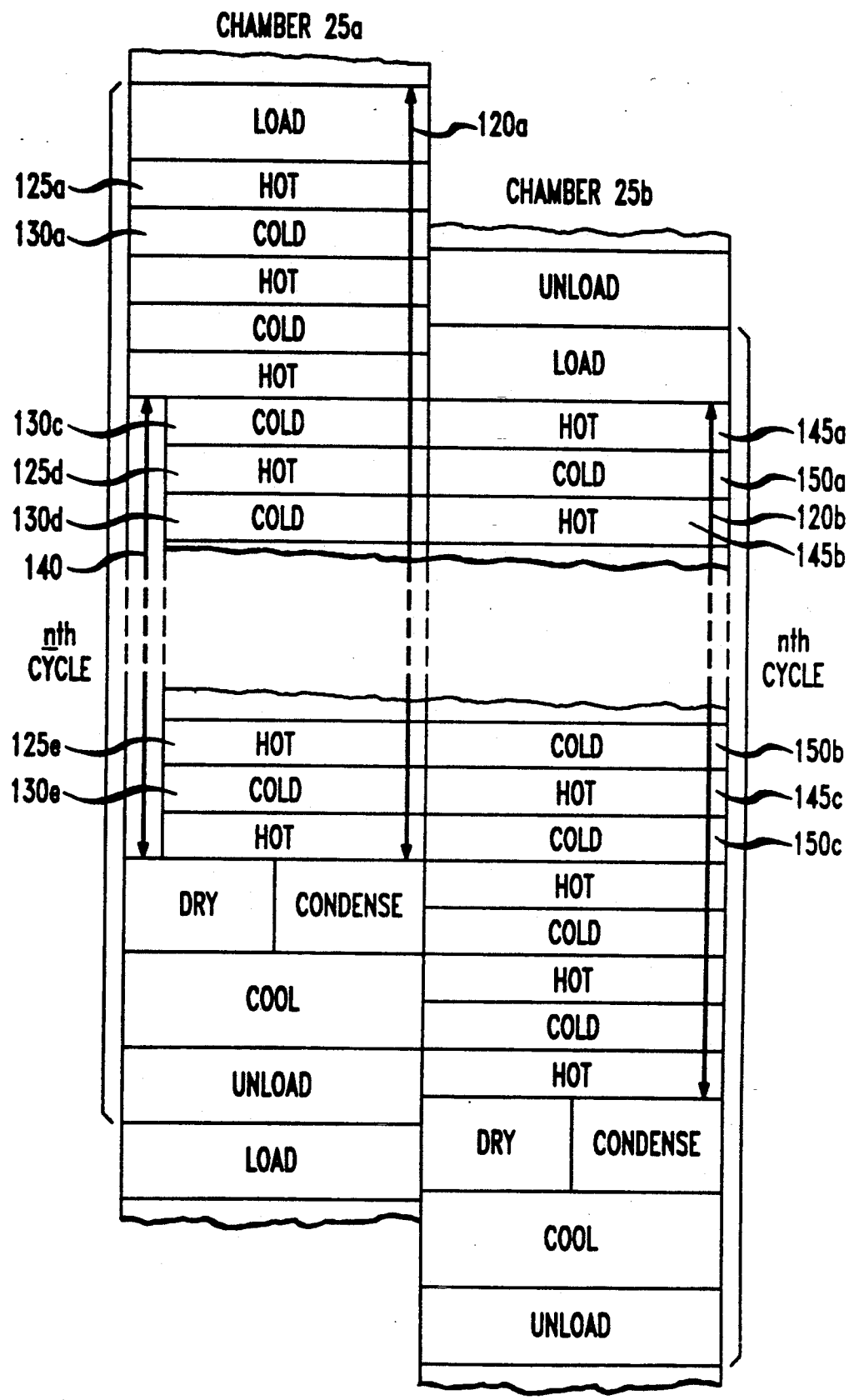
FIG. 8 is a flow diagram of a method according to the invention attained by modifying the FIG. 7 method.

The method depicted by the FIG. 8 diagram is a modification of the FIG. 7 method and differs from that earlier describeb method in that the nth cycle operation for chamber 25b lags the nth cycle for chamber 25a by less than half a cycle, the liquid contact periods 120a and 120b for those chambers have a time overlap 140, and phases of liquid contact occur simultaneously in both chambers 25a and 25b during that overlap 140. Specifically, within overlap 140, the hot phases 125 during which hot FLOURINERT is applied to the packs 23a in chamber 25a are paired in time of occurrence with cold phases 150 during which cold FLOURINERT is applied to the packs 23b in chamber 23 and, further, the cold phases 130 during which cold FLOURINERT is applied to the packs 23a in chamber 25a are paired in time of occurrence with hot phases 145 during which hot FLOURINERT is applied to the packs 23b in chamber 25b. To put it another way, within time overlap 140, the respective cycles of operation of chamber 25a and 25b became interdependent in timing in the sense that not only are there respective alternations at the two chambers, 180° between hot and cold liquid contacting the articles therein, which two alternations are 180° out of phase but, also, there are respective alternations at the two reservoirs 51 and 52, between supplying liquid to one and then the other of the test chambers 25a and 25b, such alternations for reservoir 51 and reservoir 52 being 180° out of phase.

The use of the FIG. 8 method is advantageous in instances where, in the cycles of operation for the chambers 25a and 25b, the time required in each cycle to perform the method steps included in the liquid contact period is substantially larger than the sum of the times occupied in the cycle by the other periods (i.e., the air contact period and the loading and unloading periods) since, in those instances, the conducting of liquid contact steps in both chambers during the overlap time 140 permits shortening the length of the cycle of operation for each chamber as compared to what such length would be if all liquid contact steps were to take place in only one chamber at a time as in the FIG. 7 method.

The reason why the length of such cycle of operation can be shortened is that the ability to conduct liquid contact steps of opposite phases in both chambers simultaneously and, thereby, have a time overlap between the liquid contact periods in the respective cycles for the two chambers is expedient in permitting elimination in those cycles of idle times introduced into non-liquid contact periods of the two cycles to avoid such an overlap because, say, the particular apparatus used cannot accommodate it.

FIG. 8 depicts a generalized method for operating apparatus 20 in that the relative timing between the respective cycles of operation for chambers 25a and 25b can be adjusted as desired subject only to the constraint that, inasmuch as gas handling system 100 serves both chamber 25a and chamber 25b, the air contact periods in the respective operation cycles for the chamber cannot overlap. That constraint can be fully removed by providing a separate gas handling system like system 100 for each of chambers 25a and 25b.

Such constraint can also be removed by modifying system 100 by adding to it additional ducts, duct junctions and valves controlled by unit 30 so that, under the command of that unit, air which is passed when heated through either of chambers 25a, 25b (to effect drying therein) and then through chiller 105 (to perform the condensing step) can be selectively routed to pass through the other of the chambers 25a, 25b to perform the step of cooling the articles therein, before returning to the inlet of blower 106 to start a new circulation cycle. The limiting case of shortening as described the lengths of the cycles of operations for chambers 25a, 25b by use of the FIG. 8 method is reached when the respective cycles for the two chambers are time shifted by only the amount of time required to perform the initial hot phase in the liquid contact periods of the two cycles. Such a time shift will permit the liquid contact period in each of those respective cycles to start, as is preferred with a hot phase and then will, after the occurrence of such initial phase in the leading one of such cycles, permit liquid contact steps of opposite phase to occur simultaneously in both chambers.

Figure 9:
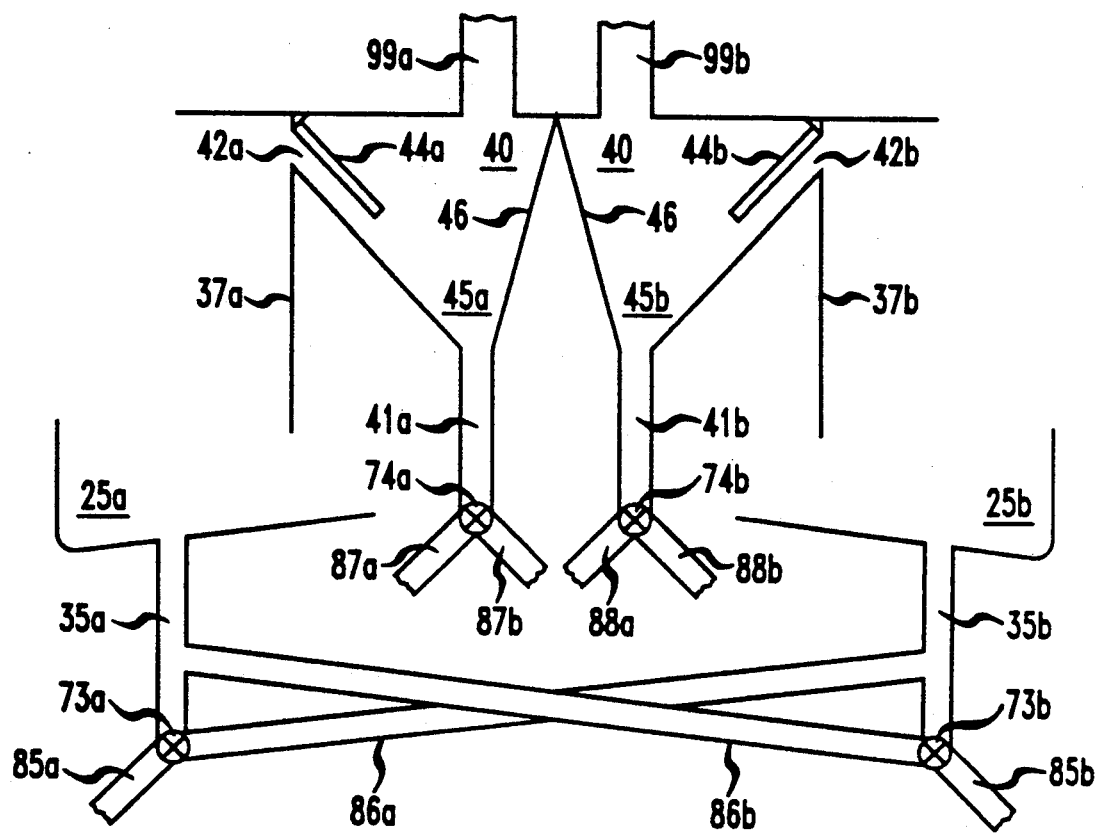
FIG. 9 is a schematic diagram showing modification made to the FIG. 2 apparatus to enable it to practice the FIG. 8 method.

FIG. 9 shows modifications which are made to the apparatus 20 to enable it to carry out the FIG. 8 method, and which are as follows. The lower portion of exhaust space 40 is divided by a partition 46 into separate drain spaces 45a and 45 for liquid from, respectively, chamber 25a and chamber 25b, and the single pipe 41 for space 40 (FIG. 2) is replaced by valves 74a and 74b each having a first port of connected to, respectively, pipe 41a and pipe 41b. Valve 74a has its second and third ports connected to pipes 87a and 87b which lead as before to the top inlets 55a and 55b of reservoirs 52 and 51. Valve 74b has its second and third ports connected to other pipes 88a and 88b which also lead, respectively to the inlets 55a and 55b.

As further modifications, the cross-connect pipe 86 (FIG. 2) is replaced (FIG. 9) by, first, a pipe 86a leading from valve 73a to feeder and pipe 35b for chamber 25b and, second a pipe 86b leading from valve 73b to the feeder and pipe 35a for chamber 25a.

Also, if gas handling system 100 is replaced by two similar respective systems for chambers 25a and 25b or is modified as described above, the partition 46 is extended upward to divide into separate halves the upper portion of exhaust space 40 as well as its lower portion, and the single gas outlet 99 for space 40 (FIG. 2) is replaced by two gas outlets 99a and 99b (FIG. 9).

The above described embodiments being exemplary only, it is to be understood that additions thereto, omissions therefrom and modifications thereof can be made without departing from the spirit of the invention. For example, liquids other than FLOURINERT can be used to environmentally stress articles in the test chambers, and some gas other than air (e.g., nitrogen) can be used to dry and cool those articles. In certain applications, the gas handling system 100 can be omitted from apparatus 20 and, if it is so omitted or replaced by two separate similar systems used, respectively, with one and the other of the test chambers, then the cycles of operation for, respectively, chamber 25a and 25b may be wholly parallel in the sense there is no shift at all, relative to each other, in the respective timings of the operation cycles for those two chambers, such parallel timing not yielding however, all the efficiencies in the use of the apparatus as do the time shifted operation cycles described above for the two chambers.

Accordingly, the invention is not to be considered as limited save as is consonant with the recitals of the following claims.

We claim:

1. Apparatus for testing articles comprising, means providing first and second chambers for containing separate bodies of fluid and for receiving said articles, first and second sources outside said chambers of liquid in hot form and cold form, respectively, liquid handling means comprising piping coupling each of said sources with each of said chambers, pumps disposed in said piping and responsive to control signals to be activated to thereupon produce flows of said liquid through said piping between said sources and chambers, valves in said piping responsive to control signals to be set to select different paths within said piping for said liquid flows, a controller unit for supplying coordinated control signals to said pumps and valves to produce intermittent flows from said first source of hot liquid into said chambers at times which are different, for, respectively, said first and second chambers, and to produce, also, intermittent flows from said second source of cold liquid into said chambers at times which are different for, respectively, said first and second chambers, and which are also different at each of said chambers than the times thereat of such hot liquid flows so as to environmentally stress articles in said chambers by alternately heating and chilling them by said liquid during test periods respective to said first and second chambers, and means to detect responses of said articles to such stressing.

2. Apparatus according to claim 1 further comprising, a source of heated gas common to both said chambers, gas handling means comprising ducting coupled between said gas source and chambers for conducting flows of heated gas from said source thereof into and through said chambers so as to remove liquid remaining in said chambers and on articles therein by converting said liquid into vapor contained in said gas, and gas flow regulating means disposed in said ducting and responsive to signals from said unit to control said gas flows to occur at different times through, respectively, said first chamber and said second chamber.

3. Apparatus according to claim 2 further comprising gas chilling means common to both said chambers and coupled thereto by said ducting to receive from said chambers said heated air with said vapor therein, said chilling means cooling such received air to convert said vapor back into liquid form.

4. Apparatus according to claim 1 in which said first and second chambers are disposed within respective enclosures on horizontally opposite sides of an enclosed exhaust space common to both said chambers, and in which said chambers have respective outlets to said space for fluid in said chambers.

5. Apparatus according to claim 4 in which said outlets are weirs disposed at the tops of said chambers and permitting flow thereover of liquid in said chambers into said space.

6. Apparatus according to claim 5 in which said apparatus further comprises gas handling means to flow gas into and through said chambers at times which are after their respective test periods, and in which said outlets from said chambers serve as outlets to said exhaust space both for said liquid and said gas.

7. Apparatus according to claim 6 in which said first and second chambers have respective inlets for said gas, and in which said gas handling means comprises ducting providing both a central path for gas flow extending between said exhaust space and a junction and, also, a pair of side paths for gas flow extending from said junction to respective ones of said inlets, and in which a chiller, a blower and a heater for said gas are coupled in said path in the order named from said exhaust space to said junction, said blower being oriented to produce flow of said gas from said space through said central path to said junction and from said junction to said inlets, and means responsive to signals from said unit to limit said gas flow from said junction to flows at different times through one and the other of said side paths to their respective inlets.

8. Apparatus for testing articles comprising, means providing a test chamber for receiving said articles, means for environmentally stressing articles in said chamber by pumping therein liquid which is alternately hot and cold to alternately heat and chill said articles during a test period therefor, means to detect responses of said articles to said stressing thereof, a source of heated gas, and gas handling means comprising ducting coupling said chamber and source to produce through said chamber after said period a flow of said heated gas which removes liquid remaining in said chamber and on articles therein by converting said liquid into vapor contained in said gas, said chambers having an inlet and outlet for said gas which are on opposite sides of said chamber and are diagonally offset from each other to produce flow of said gas in a diagonal path through said chamber, and said articles being circuit packs held when in said chamber by a test fixture disposed in said chamber and having a backplane to which said packs are electrically connected, said apparatus further comprising means in said chamber to support said test fixture so as to interpose circuit packs held thereby in said diagonal path; and so said backplane is below and to one side of said path and is at a slant to the horizontal to facilitate drainage of liquid from said articles.

9. Apparatus according to claim 8 further comprising a chiller for said gas incorporated in said gas handling means to receive said heated gas after it has passed through said chamber and to chill said received gas so as to convert said vapor therein back into liquid form.

10. Apparatus according to claim 9 in which said source of heated gas comprises a blower and a heater for said gas, and in which said chiller, blower, heater and chamber are coupled in said gas handling means in a closed loop so as to produce flow of said gas around said loop with said gas passing through said chamber, chiller and heater in the order named.

11. An article testing method comprising, loading a plurality of articles into first and second chambers for containing separate fluid bodies, intermittently contacting said articles in said chambers with hot liquid provided by a source therefor outside said chambers and common to both chambers at times for such hot contacts which are different for, respectively, said first and said second chamber and intermittently contacting said articles in said chambers with cold liquid provided by a source therefor outside said chambers and common to both outside said chambers and at times which are different for, respectively, said first and said second chambers, and which are also different at each chamber than the times thereat of said intermittent contacting of articles therein by said hot liquid so as, thereby, to environmentally stress aid articles by alternately heating and chilling each of them by said liquid during respective test periods for said two chambers, and detecting during said periods responses of said articles to said stressing.

12. A method according to claim 11 further comprising contacting said articles in said chambers after said test periods therefor by hot gas provided by a source of heat for said gas common to both chambers at times which are different for, respectively, so first and second chambers so as dry said articles of liquid remaining thereon by converting said liquid into vapor contained in said gas.

13. A method according to claim 12 further comprising passing said hot gas, after it has contacted said articles through a source of cold common to both said chambers so as to chill said gas and convert said vapor contained in said gas back to liquid form.

14. A method according to claim 13 in which said gas is circulated in closed loops which are respective to said chambers, and which loops each include said source of cold and source of heat, said gas flowing in each loop through, in the order named, such source of heat, said source of cold and the chamber included in that loop.

15. A method according to claim 12 in which said step of drying said articles is followed by the step of contacting said articles in said chambers by chilled gas provided by a source thereof common to both chambers so as cool articles therein down to room temperature.

16. An article testing method comprising, alternately applying liquid in hot form and liquid in cold form to an article in a receptacle so as to environmentally stress said article by alternately heating and chilling it by said liquid during a test period therefor, measuring a response of said article during said period to said stressing thereof, and contacting said article in said receptacle after said period by hot gas so as to dry said article by converting liquid remaining thereon into vapor contained in said gas, said method further comprising contacting said dried article with chilled gas so as to cool said articles in said receptacle.

17. A method according to claim 16 further comprising subsequently chilling said hot gas containing said vapor so as to convert said vapor back into liquid form.

* * * * *